US 6,646,556 B1

(12) United States Patent
Smith et al.

(10) Patent No.: US 6,646,556 B1
(45) Date of Patent: Nov. 11, 2003

(54) APPARATUS AND METHOD FOR REDUCING THE RISK OF DECUBITUS ULCERS

(75) Inventors: Toby E. Smith, Broken Arrow, OK (US); Craig L. Cooper, Tulsa, OK (US)

(73) Assignee: Bed-Check Corporation, Tulsa, OK (US)

( * ) Notice: Subject to any disclaimer, the term of this patent is extended or adjusted under 35 U.S.C. 154(b) by 73 days.

(21) Appl. No.: 09/591,887

(22) Filed: Jun. 9, 2000

(51) Int. Cl.[7] .............................................. G08B 23/00
(52) U.S. Cl. ..................... 340/573.1; 340/666; 340/667
(58) Field of Search ............................. 340/573.1, 529, 340/309.15, 666, 667, 309.16, 309.7

(56) References Cited

U.S. PATENT DOCUMENTS

| | | | | |
|---|---|---|---|---|
| 6,014,346 A | * | 1/2000 | Malone ................... | 340/666 X |
| 6,030,351 A | * | 2/2000 | Schmidt et al. ............. | 600/592 |
| 6,129,686 A | * | 10/2000 | Friedman ............. | 340/573.1 X |
| 6,287,253 B1 | * | 9/2001 | Ortega et al. ........ | 340/573.1 X |
| 6,320,510 B2 | * | 11/2001 | Menkedick et al. ..... | 340/573.1 |

FOREIGN PATENT DOCUMENTS

| | | |
|---|---|---|
| EP | 0853918 A2 | 7/1998 |
| GB | 2235776 A | 3/1991 |
| GB | 2329250 A | 3/1999 |
| GB | 2350681 A | 12/2000 |
| WO | WO 00/51541 | 9/2000 |

* cited by examiner

*Primary Examiner*—Thomas Mullen
(74) *Attorney, Agent, or Firm*—Fellers, Snider, Blankenship, Bailey & Tippens, P.C.

(57) ABSTRACT

There is provided herein a sensor for use in patient monitoring situations, wherein the level of patient motion activity is tracked for purposes of determining whether or not that patient has exhibited sufficient activity to merit eliminating a scheduled assisted relocation to a new position. The instant device broadly operates to sense the length of time since a patient has last moved from a previous sitting or lying position. If the patient has not moved during some predetermined time interval, it is preferred that the nursing staff be notified that it is time to manually reposition the patient. On the other hand, if the patient has changed position within the specified time period, the device will note that fact and inform the attending nurse or other caregiver that the patient need not be moved at the next scheduled relocation, thereby eliminating the need in some cases to rouse the patient from an otherwise sound sleep. In either case, the instant invention operates to reduce the risk that a patient will develop bed sores by helping ensure that the patient is manually moved as frequently as is medically necessary, but no more often than is actually necessary.

25 Claims, 8 Drawing Sheets

APPARATUS AND METHOD FOR REDUCING THE RISK OF DECUBITUS ULCERS

FIELD OF THE INVENTION

This invention relates generally to apparatus and methods for reducing the risk of bedfast patients developing decubitus ulcers.

BACKGROUND OF THE INVENTION

It is well known that patients who are confined to a bed or chair for extended periods of time are at risk of developing decubitus ulcers, i.e., pressure sores, or bed sores as they are more commonly known. These ulcers are often seen to develop within soft tissue that is compressed between a bed or chair surface and a patient's weight-bearing bony prominences, the compressed tissue being at least partially deprived of oxygenated blood flow. A continued lack of blood flow, and resultant lack of oxygen, can result in cell death which may be evidenced in the form of pressure sores. Pressure sores do not develop immediately, but rather form over time, with the development speed depending on a number of factors including the firmness and friction of the supporting surface against the patient's skin, the patient/ambient temperature, the amount of moisture in contact with the skin, and the health and susceptibility of the skin due to age or illness.

One venerable and generally accepted means of reducing the risk of decubitus ulcer development in bedfast patients is to turn them regularly, usually at approximately two hour intervals. For example, a patient in a back rest position might be periodically rolled to one side or the other, such motion helping to maintain blood to flow to soft tissue that is under compression. Similar strategies are employed for patients that are confined to a chair for long periods of time. Obviously, an assisted-movement strategy relies to a large extent on the vigilance of the (often harried) attending staff to insure that the patient is properly relocated. Further, it is far too easy for the busy care giver to let the time for turning the patient slip by in the press of other daily emergencies. To the extent that the caregiver is too busy or forgets to perform this service, this method can fail to achieve its purpose. Further, this sort of strategy can be counterproductive for use with the patient that has some capacity for self movement.

More particularly, the process of moving a patient to another position is admittedly disruptive to the patient and this is especially true at night, since the patient—if he or she were sleeping—will be awakened for the purpose of relocation. The typical two-hour movement interval must be observed around the clock if the method is to be effective, so it is necessary to rouse the patient—who might be sleeping soundly at the time—to make the required adjustment in position. Further, this adjustment might not have even been necessary if the patient had recently moved of his or her own volition. Thus, in many situations it would be advantageous for the caregiver to know if and when the patient last moved his or herself. Then, if the last movement were within a prescribed period of time, it might be possible to spare the patient an unnecessary interruption in his or her healing sleep. The caregiver would then relocate the sleeping patient, only if that relocation were actually required. Further, knowing which patients do not need to be moved could result in a substantial savings in labor costs, as the time that would otherwise be devoted to moving the patient that did not actually need to be moved could be productively applied elsewhere. That being said, as useful as this sort of information might be to the health care provider, however, the present state-of-the-art in patient management does not provide this sort information.

Generally speaking, there are two broad inventive approaches to dealing with decubitus ulcers: mechanical and medicinal. The mechanical approach is aimed at preventing the occurrence of bed sores through the use of a specialized mattress, pad, or other arrangement, which is designed to lessen the weight-pressure that is brought to bear on the patient's bony prominences. These devices might be either static (e.g., foam, air, or water mattresses) or dynamic (e.g., compartmentally inflatable mattresses that dynamically shift the locus of support pressure under the patient in response to the patient's movements). Examples of inventions in the prior art that are generally concerned with this subject matter are U.S. Pat. Nos. 4,425,676, 5,926,884, and 5,072,468, the disclosures of which are incorporated herein by reference.

On the other hand, the medica—or second inventive—approach is concerned with the development of medicinal compounds and methods of treating the ulcer after it occurs. This approach is obviously useful but reactive, rather than proactive, as it attempts to minimize the damage occasioned by the ulcer after it has formed.

General information relating to mats for use in patient monitoring may be found in patent application Ser. No. 09/285,956 filed Apr. 2, 1999, now U.S. Pat. No. 6,307,476, the disclosure of which is specifically incorporated herein by reference. Additionally, U.S. Pat. Nos. 4,179,692, 4,295,133, 4,700,180, 5,600,108, 5,633,627, 5,640,145, and 5,654,694 (concerning electronic monitors generally) contain further information generally pertinent to this same subject matter, as do U.S. Pat. Nos. 4,484,043, 4,565,910, 5,554,835, and 5,623,760 (switch patents), the disclosures of all of which are all incorporated herein by reference.

Heretofore in the patient monitoring arts there has been no apparatus or method aimed specifically at reducing the risk of bed sores in a semi-invalid patient, i.e., the patient who at least occasionally moves without assistance. With a semi-invalid patient, assisted repositioning—whether manual or mechanical—should only take place if the patient has not moved for some particular period of time. This, of course, suggests the need for a method and apparatus for monitoring the patient so that the time when he or she last moved can be determined. Further, the amount or magnitude of the patient's movement should also be monitored so that a repositioning will still take place as-scheduled if the patient has moved during the previous time period, but the amount of movement has not exceeded some particular threshold level (i.e., whether or not a significant relocation or movement has occurred). Finally, there is a need for an apparatus that can monitor and report the overall amount of patient self-induced and/or caregiver assisted movement, so as to give the caregiver (or that person's supervisor) some estimate of the amount of movement by the patient in the bed.

Heretofore, as is well known in the patient monitor arts, there has been a need for an invention to address and solve the above-described problems. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a sensor for use in patient monitoring situations, wherein the level of patient motion is tracked over a given period of time for purposes of determining whether or not that patient has exhibited sufficient motion to merit eliminating a scheduled assisted relocation to a new position. The instant device operates to sense the length of time since a patient has last moved from a previous sitting or lying position. If the patient has not moved during, for example, the prior two-hour period, it is preferred that the nursing staff be notified that it is time to manually reposition the patient. On the other hand, if the patient has changed position within the specified window, the device will note that fact and withhold its reminder to the nurse or other caregiver that the patient needs to be moved at the next scheduled relocation time, thereby eliminating the need in some cases to rouse the patient from an otherwise sound sleep. In either case, the instant invention operates to reduce the risk that a patient will develop bed sores by helping ensure that the patient is manually moved as frequently as is medically necessary, but no more often than is actually necessary.

In accordance with another aspect of the instant invention there is provided an electronic monitor for use with a patient sensor which is designed to monitor the patient's position and calculate his or degree of activity in the chair or bed. In the preferred embodiment, the monitor consists of a microprocessor in electrical communication with a patient sensor (discussed below). The microprocessor will be equipped to ascertain—by reference to the attached sensor—an initial position of the patient within the bed. Once an initial position is determined, the monitor will then continue to watch the patient's position, looking for "significant" changes in that position. If such a change has not occurred before the passage of some predetermined time interval, the monitor will enter into an "alarm" or signaling state. Depending on the settings selected by the operator, the monitor might emit an audible alarm, signal a nurses station, initiate a visual alarm (e.g., a flashing light), etc., that would serve warning to the caregiver that it is time to turn the patient. Needless to say, although the preferred embodiment of the instant invention calls for a device that gives notice to the care giver when the patient needs to be moved, the invention disclosed herein could as easily be modified to notify the caregiver when the patient does not need to be moved.

On the other hand, if the patient demonstrates a significant change in position prior to the expiration of the predetermined time period, the CPU in the electronic monitor will note that fact and reset the timer, preferably to its initially specified time interval. This change in position may or may not be accompanied by the sending of a signal to the care-giving staff to inform them of that fact. The CPU will then continue to monitor's the patient's position via the sensor until either the current time period expires or the patient moves again.

Broadly speaking, the instant invention consists of two functional components: a position sensor and an electronic monitor. In the preferred embodiment, the electronic monitor and sensor will be separate devices. However, it is certainly possible, and well within the skill of one of ordinary skill in the art, to combine these two functions into a single operating unit. That being said, preferably, and as described below, two separate modules will be utilized. In broadest terms, the position sensor component generates signals in response to the location or orientation of the patient in the bed or chair. The electronic patient monitor senses and interprets the signals from the position sensor and, in the preferred embodiment, handles the arming/disarming of alarms and communications with the nurses station.

The sensor portion of the instant invention, which might be any one of a number of different devices, must at minimum be capable of sensing a change in the patient's position, location, or orientation within a bed or chair. Examples of devices that might be suitable for use with this invention include a pressure sensitive bed or chair mat, a temperature sensitive bed or chair mat, pressure sensitive mats placed underneath the feet of the hospital bed, accelerometers in communication with the springs of the bed, infrared motion detectors, etc.

A minimal requirement of the electronic monitor is that it be able to sense patient position information as provided by the sensor. Additionally, it must be able to track the passage of time in at least some rudimentary fashion, so as to determine the time interval between patient movements. In the preferred embodiment, the monitor will include a microprocessor which can implement the logic described below and, additionally, can function as a clock if need be. Finally, in the preferred embodiment the monitor will be able to use the sensor information to differentiate between body movements that are only slight shifts in position and other movements that actually result in a change the patient's weight supporting points.

Turning now to various embodiments of the instant monitor, according to a preferred embodiment of the instant invention, there is provided a monitoring device substantially as described previously, but wherein a patient movement threshold is established such that only "significant" movements are sufficient to cause the device to reset withhold notification of the nursing staff to turn the patient, thereby letting the patient continue to rest.

According to a further preferred aspect of the instant sensor, there is provided a monitoring device substantially as described previously, but wherein a patient movement threshold is established as described previously, but wherein the "significant" movement must be maintained for some period of time. That is, if a patient moves significantly, but that movement is only temporary (e.g., for less than ten minutes), after which the patient returns to nearly the same position, the monitor will not be reset, and the staff will be called to turn this patient on the normal schedule.

According to another aspect of the instant invention, there is provided a patient monitor substantially similar to that described above, but wherein the accumulated timed movement of the patient is monitored. Thus, if the patient is sufficiently restless but no single movement event amounts to a significant relocation, that patient might still not need to be turned as they have not accumulated enough time in any one position to cause a problem. A preferred embodiment of the instant invention will detect and respond to that sort of condition.

According to still another aspect of the instant invention, there is provided a patient monitor substantially similar to that described above, but wherein the motion time interval (i.e., "turning time", hereinafter) is not a fixed interval but is adjustable according to parameters specified by operator. Many other variations are possible and have been contemplated by the instant inventors.

In the preferred embodiment the sensing device will be a pressure-sensitive bed mat which is placed underneath a weight-bearing point of the patient. The mat will preferably be designed to sense at least one point of contact along its length, i.e., it will be able to determine the distance from one of its ends to the nearest point where the patient's weight compresses the mat. Obviously, for a completely motionless patient, this parameter (distance-to-contact-point) will be unchanging. However, if the patient rouses and moves, the point of contact will change—at least during the time that the patient is moving. It may be that the patient will completely remove his or her weight from the mat before settling back down again. If the patient is out of bed for more than a brief time that would typically be sufficient reason to reset the movement timer. However, the more likely scenario it that the patient will simply roll from one side to the other without ever completely removing weight from the mat. In that case, the monitor will note the change in patient position-as measured by the change in distance to nearest contact point—and, depending on its parameter settings, determine whether that movement is significant and, thus, merits resetting the movement timer. Finally, it should be noted that one advantage of using a mat-type arrangement as described here is that the mat can then double as an exit mat, if that is desired.

According to a further embodiment, there is provided an electronic monitor as described above, but wherein the electronic monitor begins to sound a local warning a predetermined amount of time before it signals the nurses station. That is, in the preferred variation of this embodiment the electronic monitor might begin to make a relatively unobtrusive noise such as a chirp or beep (say) five minutes before the nurses station was to be notified. This noise might be enough to rouse the patient so as to cause him or her too turn without assistance. On the other hand, if the patient does not move at the predetermined time the nurses station will be signaled. This embodiment has the advantage of helping patients to learn to turn themselves.

The foregoing has outlined in broad terms the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to cover all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

According to a preferred aspect of the instant invention, there is provided a monitor and sensor, wherein the sensor is configurable to sense a position of a patient in a bed, chair, etc., and be responsive to changes therein. The electronic monitor, which is preferably kept in continuous electrical communication with the sensor, tracks the status of the sensor and responds according to its pre-programmed instructions when a patient moves or when a patient does not move for some period of time.

PREFERRED ELECTRONIC MONITOR EMBODIMENTS

Figure 1:
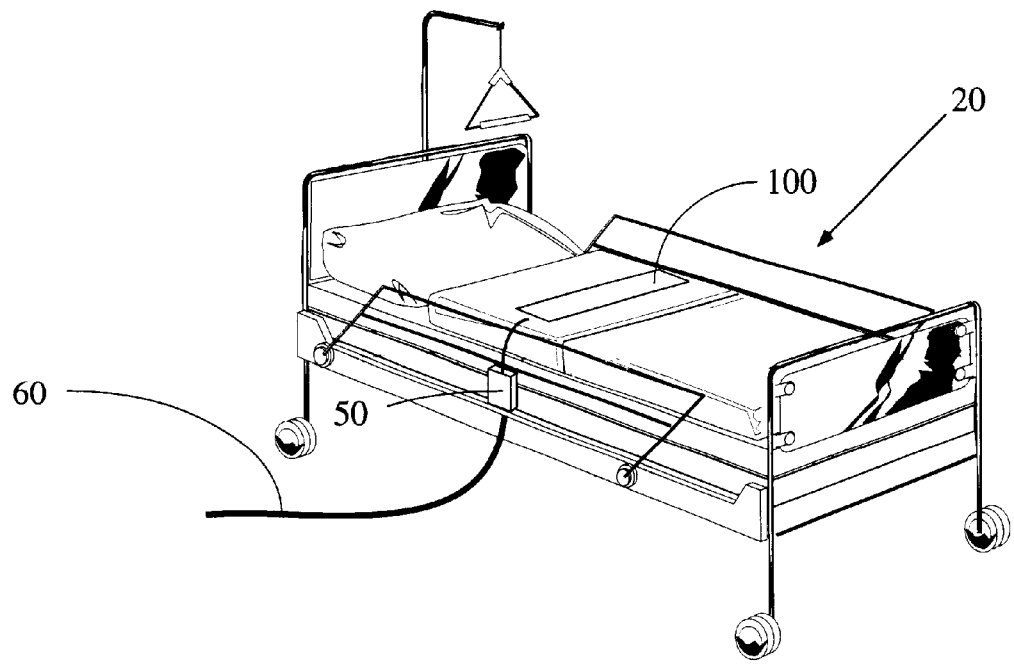
FIG. 1 illustrates a preferred embodiment of the instant invention as it would be used on a bed.

As is illustrated in FIG. 1, in the preferred embodiment the instant invention utilizes both an electronic patient monitor 50 and a sensor 100. The function of the electronic monitor is to track changes in patient position (as measured by the sensor) and act on those changes according to its pre-programmed instructions (e.g., FIG. 4). Note that the monitor might be battery powered or supplied with external power. Either configuration would be suitable for use with the instant invention.

Figure 3:
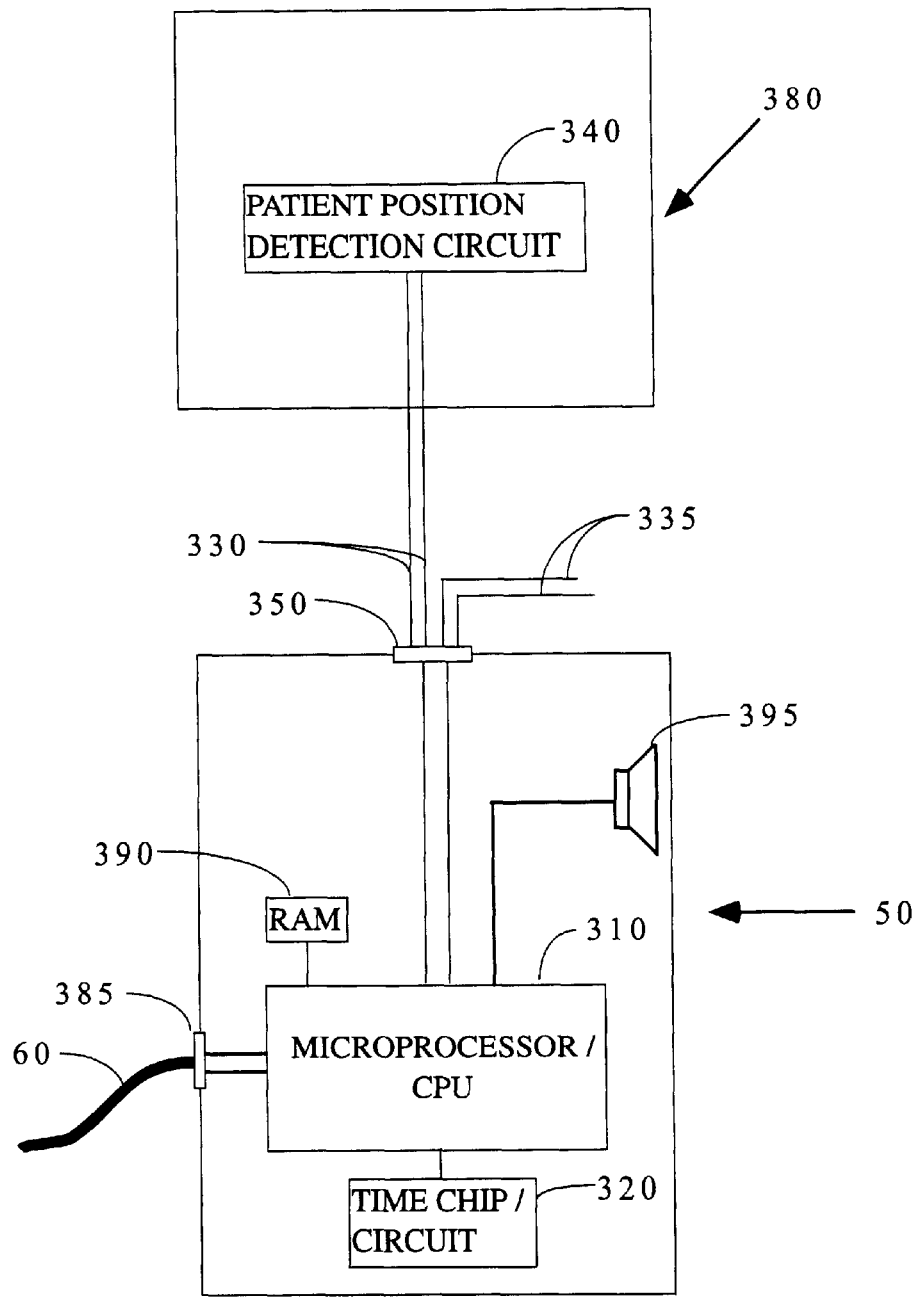
FIG. 3 contains a schematic drawing of a preferred monitor/sensor arrangement.

FIG. 3 contains a schematic illustration of a preferred monitor 50/sensor 380 arrangement. In the preferred embodiment, the monitor 50 will contain at least one microprocessor/CPU 310 for the execution of pre-programmed instructions. The CPU 310 is in electronic communication with the patient detection/position circuit 340, preferably through connector 350. In the preferred embodiment, the interconnecting wire will contain at least four electrically isolated leads: 330 and 335. Although only two such electrical lines 330 are strictly necessary to sense the patient's position, it is conventional to use a four-element wire. The other electrical lines 335 are available for other purposes.

Connector 385 is provided to allow the microprocessor 310 to send a signal to a remote receiver such as a nurses station, if that is needed. In the preferred embodiment, a connecting wire 60 will connect the monitor 50 to the nurse call network, which is conventionally accessed by way of a wall-plug. Of course, it is envisioned that an alarm might be sounded locally (e.g., from an audio speaker 395 that is preferably built into the monitor) in addition to (or instead of) notifying the nurses station. When the monitor 50 is placed on a wheel chair, a local alarm may be the most practical solution. For purposes of the instant disclosure, the term "alarm" will be used in its broadest sense to refer to a local or remote speaker, flashing light, pulsating signal (e.g., of the sort used in conventional pagers) or similar signaling mechanisms which are responsive to commands from the CPU 310 and which can be used to obtain the attention of a caregiver. Of course, a "speaker" includes without limitation piezoelectric devices capable of generating an audible alarm signal. Thus, when the term "speaker" is used hereinafter, that term should be construed in the broadest possible sense to include any device capable of emitting an audible alarm signal under the control of the microprocessor 310. Additionally, when speaker is used herein that term should also be taken to include an associated power amplifier to drive it, if one is necessary (as it often will be). Finally, it should also be noted that it is not an essential element of the instant invention that the speaker 395 be found within the body of the monitor. The speaker 395 could also be mounted externally thereto, and, as an extreme example, might by located in an adjacent hallway or at the nurses station.

Additionally, the connecting wire 60 might be used to place the CPU 310 in electronic communication with any number of other remote devices, including remote networks, computers, etc. Alternatively, it is known in the art to provide the electronic monitor 50 with additional communications hardware including, for example, a serial port, a parallel port, a USB port, a fire wire port, an infrared communications port, etc., all of which would preferably be accessible by the microprocessor 310.

Figure 4:
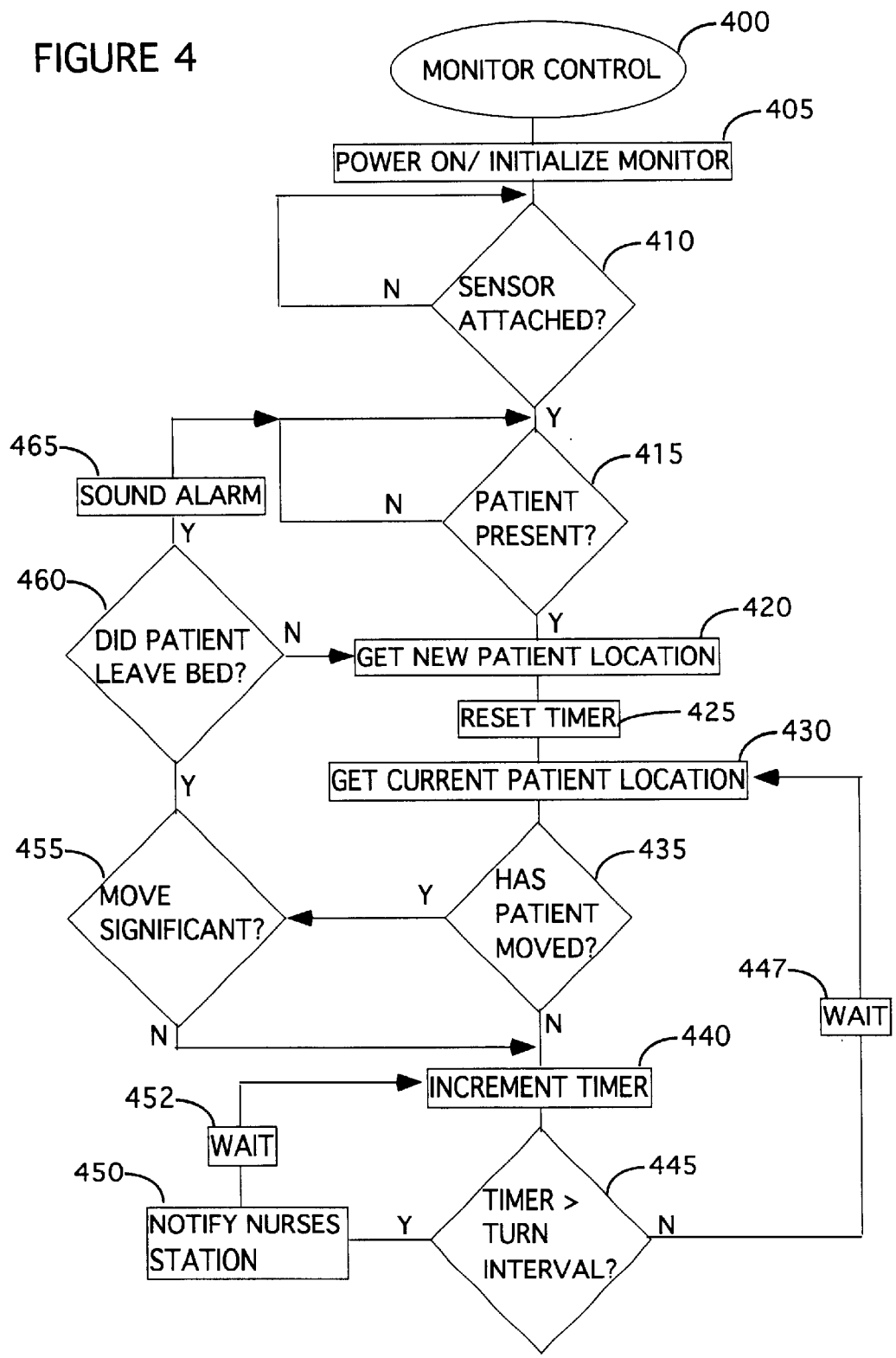
FIG. 4 is a flow chart that illustrates a preferred logic for use with the electronic patient monitor.

FIG. 4 contains a preferred logic for use with the CPU 310. As is indicated in that figure, at power-up the CPU 310 will typically initialize various internal variables (step 405), perform internal quality control checks, check to see if a sensing device is attached (step 410), etc. This is all done in preparation for normal operation. As a next preferred step, the CPU 310 will attempt to determine whether or not a patient is present in the bed, chair, etc. This might be done many ways, but in the case where the sensor is a pressure sensitive bed mat 100 or chair mat 200 this step 415 is easily accomplished by checking to see if the patient's weight has "closed" the switch. Of course, exactly how the monitor 50 might make this determination 415 will depend on the sort of sensor that is used.

As a next preferred step, the CPU 310 will query the sensor to determine the patient's initial position (step 420). Again, exactly how this is determined will depend on the sensor that is used: some specific examples will be discussed below. The initial position will be stored—preferably in the monitor's RAM 390—for later use. Needless to say, the term RAM should be interpreted in its broadest sense to include any sort of volatile or nonvolatile storage that can be accessed by a microprocessor.

In the preferred embodiment, the CPU 310 will next determine the patient's then-current location (step 430). As will be described hereinafter, the exact method by which the patient's position is determined is dependent on the choice of patient sensor. However, for purposes of the instant monitor embodiment, it will assumed that the patient's position is available as a measure of the distance from the edge of a bed mat to the nearest point where the patient's body weight compresses the two halves of the mat into contact.

Preferably, the timer will next be reset (step 425) to zero, signifying the start of a new time measurement period. As is conventional in these sorts of timing devices, the timer will be incremented at intervals 425 corresponding to the frequency at which the CPU 310 checks the patient's status. Obviously many alternative arrangements are possible, including direct time interval calculations from successive calls to a time chip/circuit 320, i.e., by "subtracting" an earlier clock time from a later clock time. Additionally, it should be noted that it is not necessary to equip the instant monitor 50 with a true "time chip" as that term is understood to those skilled in the art but, instead, the CPU 310 can be instructed to "count time" by repeatedly performing an operation whose time duration is at least approximately known (e.g., incrementing the value of an integer variable). Thus, in the text that follows reference to a "time circuit" or "time chip" should be construed as broadly as possible to include discrete hardware for determining time, as well as timing loops that are performed within the CPU 310. Those skilled in the art will recognize that there are a multitude of ways to accomplish the general goal of determining a time since a patient last moved.

As a next preferred step, the CPU 310 determines the then-current position of the patient (step 430). By comparing the most recently determined position 430 with the initial position 420 established previously, it will be possible to determine whether or not the patient has moved since the earlier reading was taken (step 435). Of course, the preferable way of making this determination is to subtract (difference) the numerical value corresponding to the current patient position from the numerical value corresponding to the initial patient position. A non-zero difference indicates that the patient has adjusted his or position or moved. More generally, there are many ways of producing a differential movement measure that do not require subtraction, although that is the preferred embodiment. For example, taking ratios of the two location values would also have some utility. Even more generally, comparisons could be based on the actual signals received from the location sensor 100 rather than converting those signals into to actual distances or locations. Thus, if the sensor 100 determines patient location from, say, the measurement of capacitance, mathematical or logical operations might be performed directly on the sensed capacitance values themselves to produce a differential movement measure which is correlated with patient movement.

If the patient has not moved since the initial determination of his or her position, the timer is preferably incremented 440 and compared with the pre-determined turn interval (step 445), the amount of increment preferably being related to the amount of time that has transpired since the last time the patient's location was checked.

As a next preferred step, the amount of elapsed time is compared with the predetermined turn interval (step 445) as specified by the physician or other care giver. If the elapsed time is less than the predetermined interval, then CPU 310 then preferably waits (step 447) before checking the current patient location again 430. Of course, the amount of time that the CPU 310 delays before getting the next patient location 430 might be any amount from zero to several minutes, with the preferred amount of delay 447 being several seconds.

In the event that the timer exceeds the turning interval specified by the user of the instant invention, a caregiver is preferably notified 450. It would be expected that the patient turn interval would be an adjustable parameter that is set by the care giver and would typically be specified by the patient's physician and might be, for example, about two hours. This means that the patient would normally need to be turned every two hours, unless the patient first turns him or herself.

In the event that the elapsed time exceeds the preset turning time interval, in the preferred embodiment the nurses station 450 will be notified. Alternatively, an alarm might be sounded from a speaker 395 built into the monitor 50, a light might be flashed on the unit 50, a light might be flashed in the hall outside of the room, or any number of other steps might be taken to notify the care giver that it is time to turn this particular patient. Any number of alternative means might be used to signal the care giver and those skilled in the art are well able to devise many such signaling arrangements.

Additionally, and as a further preferred embodiment, it is preferable that the timer continue to accumulate time until the patient is actually moved by the staff (steps 452, 440, 445, and 450). By continuing to monitor the patient's condition—and noting the elapsed time since the nurses station was notified—while the patient is awaiting turning, some measure can be obtained of the responsiveness of the staff to the patient's needs. As before, the amount of time that the CPU 310 waits (step 452) may be selected by the programmer and/or the care giver. Additionally, it is anticipated that it might be necessary in some instances to send more than one notice to the nurses station 450 depending on the length of time that it takes for the staff to respond, and steps 452, 440, 445, and 450 allow for and implement that as a possibility.

Turning now to the case where the patient has changed position, in the preferred embodiment a further step 455 is taken to determine whether the move was "significant." If the move was not significant, the timer is not reset and continues to accumulate time 440. The purpose of this step is to prevent the timer from resetting in those instances where the patient has only shifted position slightly, e.g., if they briefly rolled to one side but then immediately returned to their original position. In that case, it might not be advisable to reset the timer, because the region of the patient's body that was at risk is still so. Obviously, the time interval during which the patient moved from the original position, as well as amount of movement, could both be monitored and either (or both) could be used to determine whether a move was significant. For example, it might be desirable to flag as "significant" only those location changes that persisted for, say, over ten minutes, i.e., the patient maintained the new position for at least ten minutes before returning to his or her original position. In other cases, a significant move might be measured in inches, e.g., say a horizontal movement of five inches or more. Additionally, significant movements might be limited to those cases where the patient moved several inches and maintained that position for more than a few minutes. Finally, it may be the case that the patient is restless and has performed a number of small relocations, none of which might amount to a significant move. However, when these moves are considered in concert, they could obviate the need to turn the patient. In that case, the cumulative amount of motion of the patient might be calculated over some time period to see if a suitable composite activity level has been achieved, the analysis potentially combining the clock-time each (non-significant) movement took place, the distance that the patient moved, and the amount of time the patient remained in each position, etc. Obviously, the movement history of the patient might be accumulated locally in RAM 390 or stored remotely, if the appropriate computer networking connections are available. The motion level trigger could further be customized to reflect the sort of illness or injury that the patient is being treated for. Obviously, many variations on this basic idea are possible and have been specifically contemplated by the instant inventors.

However, in the event that the most recent move (or the general motion level of the patient over time) is deemed significant, a next preferred step 460 is to check to see if the patient has left the bed. In the event that the sensor is a bed mat (e.g., 100) it would be a simple matter to use the CPU 320 to determine whether the circuit was "open" (e.g., a pressure sensitive mat was not "compressed" by the patient's weight), and, thus, the patient had apparently left the bed. Indeed, this is the preferred embodiment of the instant invention: a bed mat 100 that can also be used to sense a patient's position thereon. With other sorts of sensors, other methods of determining whether the patient has left the bed are available. Some of the preferred ways will be discussed below.

If the patient has not left the bed, the preferred next step is to get a new patient location 420 and save that value for comparison against future movements. Additionally, it would be appropriate to reset the timer before entering the patient checking loop (i.e., steps 435, 440, 445, 447, and 430).

However, if the patient has left the bed 460, it is preferred that the patient monitor notifies the caregiver of that fact through the use of a signal that is sent to the nurses station (step 465). In the event that the patient has been deemed unable to leave the bed for health reasons, this signal will alert the nurses that they should check on this patient. Alternatively, the electronic monitor 50, if it is equipped with a speaker as many such monitors are, might sound a local alarm. Obviously, many variations of this basic arrangement are possible and have been contemplated by the instant inventors.

Turning to another aspect of the instant invention, there is provided an electronic monitor substantially as described above, but wherein a pre-alarm signal is initiated locally at the monitor 50 beginning some predetermined period of time before the turn interval expires. In more particular, it is anticipated that in some instances it might be desirable to have the monitor 50 begin to sound some sort of "alarm" before the expiration of the turn interval to encourage the patient to move on his or her own. The patient, if he or she is in a condition to hear and respond to the sound, will be thereby encouraged to move to a new position so that it will not be necessary for the staff to manually relocate him or her. In the preferred embodiment, the sound that is generated will be a relative unobtrusive noise such as a "chirp" or low "beep", a sound that would be sufficient to notify an "alert" patient but that would not unduly disturb a resting patient and that would not disturb patients in adjoining beds or rooms. Preferably, the alarm will come from a speaker 395 which has been made a part of the monitor 50. Of course, many alternative arrangements are possible, including having the pre-turn alert come from a remote speaker. This alert could also take the form of a flashing light or other standard signaling mechanisms, however preferably sound will be used.

PREFERRED SWITCH EMBODIMENTS

Mat Embodiments

Figure 7:
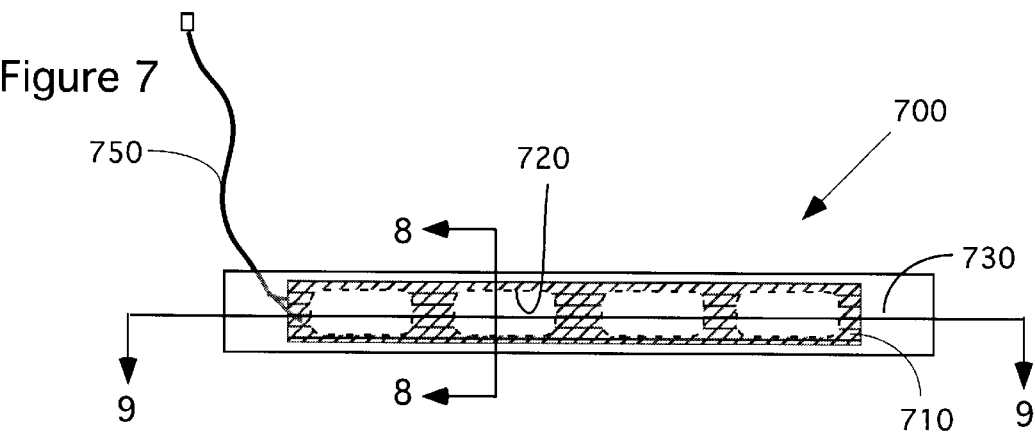
FIG. 7 illustrates the major components of a pressure sensitive mat.
Figure 8:
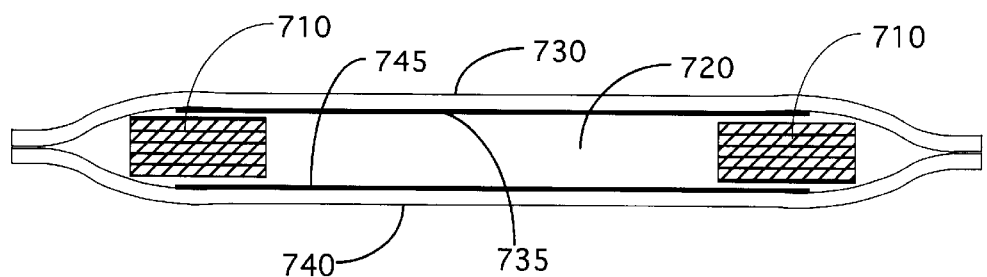
FIG. 8 contains an illustration of a transverse cross section of the mat of FIG. 7.

Turning first to FIG. 1 wherein the general environment of the instant invention is illustrated, in a preferred arrangement a pressure-sensitive sensor 100 is placed on a hospital bed 20 in an area of the bed that would be expected to bear the patient's weight. Generally speaking, and according to a first preferred embodiment, the mat 100/monitor 50 combination works as follows. As is illustrated in FIGS. 7 and 8, a typical pressure sensitive mat contains an inner non-conductive layer 710 which is "sandwiched" between two outer flexible non-conductive layers 730 and 740 which are conventionally made of some sort of thin plastic-like material. Cut into the central spacer 710 are one or more apertures 720 which are sized so as to allow the inner faces 735 and 745 of the outer members 730 and 740 to come into contact when weight is placed on the mat 700. It is conventional to treat the inner surfaces 735 and 745 with an electrical conductor of some sort (e.g., conductive-based ink, vacuum deposited metal or other conductive material, etc.) so that an attached patient monitor 50 can determine whether or not the two faces 735 and 745 have come into contact by means of a simple continuity check through electrical leads 330.

Figure 9A:
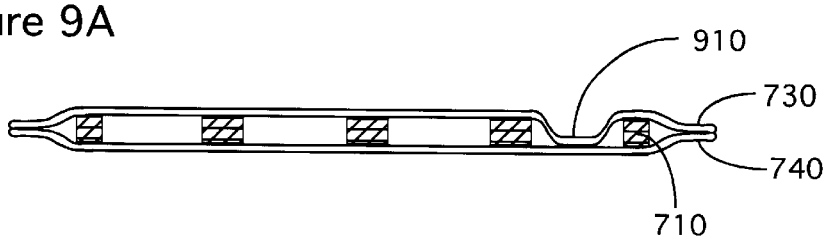
FIG. 9 contains a longitudinal cross section of the mat of FIG. 7 after weight has been applied to the mat at different locations.
Figure 9B:
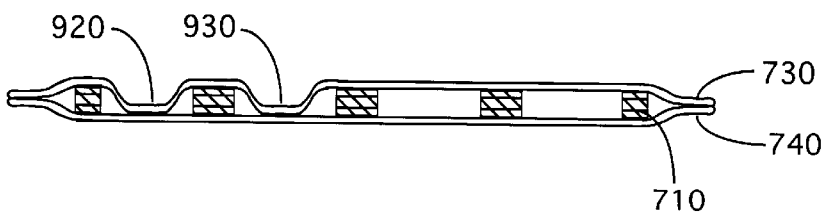

As is illustrated in FIGS. 9A and 9B, the inner faces 735 and 745 will come into contact at different locations, depending upon where pressure has been placed on the mat 700. For example, FIG. 9A represents a situation where the patient's weight rests near the right-most end of the mat 700 which produces a contact point 910. On the other hand, FIG. 9B illustrates a case where a patient's weight is spread about near the left end of the mat 700, which results in contact points 920 and 930.

For purposes of the instant embodiment, it is desirable to measure at least the distance from, say, the left end of the mat (the end nearest the electrical line 750) to the nearest point where the patient compresses the mat into contact. Changes in the value of that measurement will reflect changes in the position of the patient on the mat 700 and in the bed.

The distance to the nearest contact point might be determined in many ways. In the event that the mat is a conventional pressure sensitive mat, the distance to the nearest contact point might be determined, for example, by measuring the resistance in the patient detection circuit, with lower resistances being associated with contact points nearer the entry point of the electrical line 750. As another example, a voltage pulse could be sent into the mat and the time until its return noted—contact points being more distant will result in longer transit times for the voltage pulse. "Longer" of course, would necessarily be measured in pico-seconds. As still another example, the capacitance of the patient circuit could be measured, with higher capacitances being associated with more contact area between the patient and the mat. As a further example, it is possible to induce an oscillation in the patient detection circuit, where the frequency of the induced oscillation is indicative of the patient position. Those skilled in the art will recognize that these sorts of methods, and many others, could be used to sense the patient's position on a conventional unmodified pressure sensitive mat.

Figure 10A:
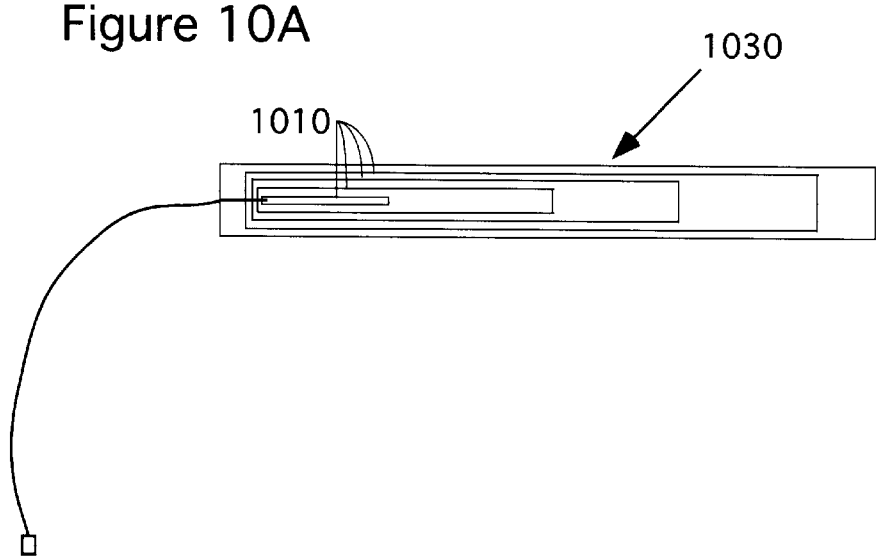
FIG. 10 illustrates some mat-type sensors that would be suitable for use with the instant invention.

According to another preferred embodiment, there are provided mat-type patient position sensors that are constructed especially for the purpose of determining the location of the patient thereon. As is generally indicated in FIG. 10, there are many ways that such a mat might be constructed. As a first example, in the embodiment of FIG. 10A a patterned conductive array 1010 has been applied to the inner surface of the non-conductive outer mat member 730 of a pressure sensitive mat 1030. By evaluating the continuity of the different pattern elements 1010 it is possible to determine location of the weight bearing portion of the patient nearest the left terminus of the mat.

Figure 10B:
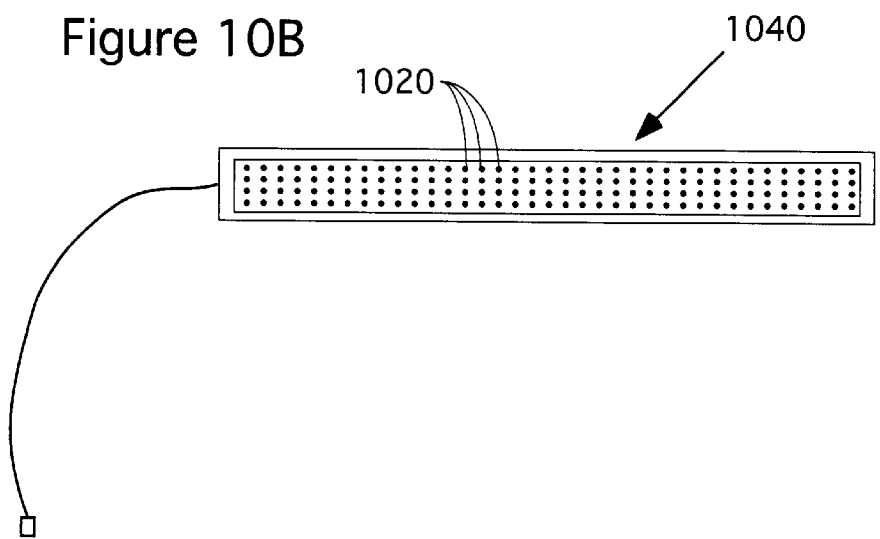

As a second example, the embodiment of FIG. 10B illustrates that a grid of individual sensor points 1020 might be used to more precisely determine the location of the patient. By separately monitoring the status of each of the sensor points 1020 in mat 1040, it will be possible to accurately determine the location of the patient who is positioned thereon. Note that these sensors might be part of a pressure sensitive mat, in which case they could be electrically conductive "points" 1020 that would exhibit continuity when pressure from the patient's weight moved the illustrated mat-half into contact with another conductive surface. However, more generally these sensors could be temperature sensors (warmth at a temperature sensor being indicative of a patient location) or any other sort of sensor that would respond when the patient was proximate thereto. Preferably, each of the sensor points 1020 would be separately readable by the CPU 310, so that the patient's position could be accurately determined at any point in time.

As still another example, the mat might be manufactured in the form of a sealed tube or pillow containing air or some other gas. As the patient moves and shifts his or her weight on the mat, pressure differences will be produced. By monitoring the pressure of the gas within the mat, it is possible to determine when the patient changes position and, thus, whether or not he or she needs to be turned.

As another example, inductance-based position determination may also be used with a mat-type embodiment. As should be clear to those of ordinary skill in the art, the inductance exhibited by a mat will vary depending on the position of the patient on the mat and the contact area between the patient and the mat. Thus, by continuously measuring inductance it is possible to track patient motion in the bed, chair, etc. The precise method by which inductance changes are related to the patient's motion will depend on a number of mat parameters and may need to be determined empirically for each type of mat.

As a further example, the instant inventors contemplate that a grid of piezoelectric elements might be placed within a mat-type sensor in a regular pattern generally similar to that of FIG. 10A. Of course, it is well known that piezoelectric materials generate an electrical current when stressed, so it is possible to locate the patient on the mat by determining which of the various piezoelectric elements in the grid is currently experiencing stress in the form of weight/pressure from the patient. Needless to say, if the patient moves and thereby changes his or her weight distribution on the mat, the particular elements that are stressed will change, thereby giving an indication of the patient's new position.

Figure 12A:
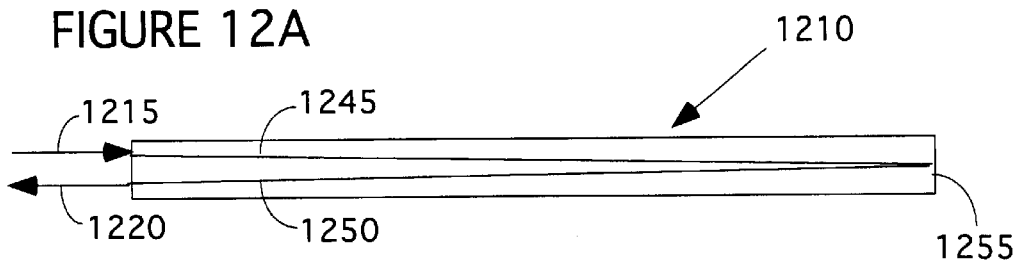
FIG. 12 contains a schematic illustration of a preferred sensor which utilizes an optical source to determine patient position.

Turning now to FIG. 12 wherein other preferred embodiments are presented, FIG. 12A indicates generally how an optical source 1215 can be used to determine a patient position. Preferably, the device 1210 will be oriented transverse to the direction the patient is laying and the patient thereafter placed thereon. The device 1210 might be, for example, a film, a sheet, or tubing of an internally-clear material such as plastic that is elastically deformable and which is at least partially reflective to light at its end 1255. In this embodiment—which is shown in FIG. 12A without a patient being present thereon—light energy 1215 is introduced into device 1210 at one end. Light then travels through the apparatus 1210, is reflected at its remote terminus 1255 and returns 1250 to the originating end where it emerges as measurable light energy 1220. FIGS. 12B and 12C indicate how the instant embodiment works when a patient is present and resting on the device 1210. In these figures, depression 1225 marks where the weight of a patient bends the device 1210. At least some of the light rays 1290—and in some cases substantially all of such light rays—that formerly traveled to the end of the device 1210 and were reflected 1295, now are intercepted and reflected by the curve 1225 induced by the patient's weight. The net result is that the returning light energy 1295 will be measurably changed because it has traveled a shorter distance through the attenuating medium of the apparatus 1210. Thus, the brightness of the emitted/reflected light energy is a measure of the distance that the light has traveled, which corresponds to the closest point at which the patient depresses the device 1210. Similarly, if sensitive enough measurements are made, it will be seen that the time for light to be reflected and return is shorter in the case of FIG. 12B than in the undeformed embodiment of FIG. 12A. Thus, the time to travel through the embodiment 1210 and return to the point of origin is also a measure of the point of nearest compression. (By way of example only, this transit time might be measured via time domain reflectometry/timed differencing).

Figure 12B:
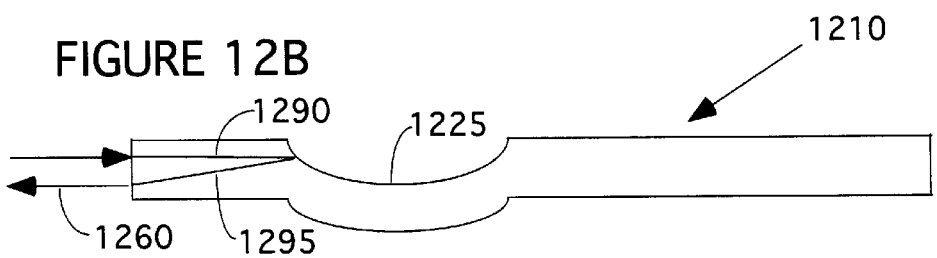
Figure 12C:
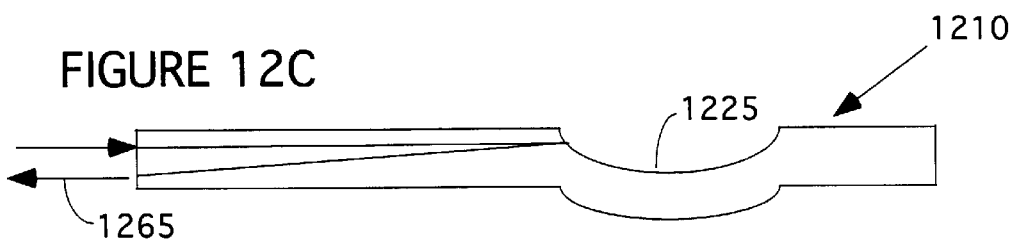

Similarly, the example of FIG. 12C would exhibit higher attenuation than the example of FIG. 12B and lower attenuation than the example of FIG. 12A. Thus, the amount of attenuation (or brightness of the emerging reflected light 1220, 1260, and 1265) can be used to provide estimates of the patient's current position. Finally, the same result holds with respect to transit times, with the transit time of the emerging light energy 1265 being longer than the example of FIG. 12B and shorter than the example of FIG. 12A.

Figure 12D:
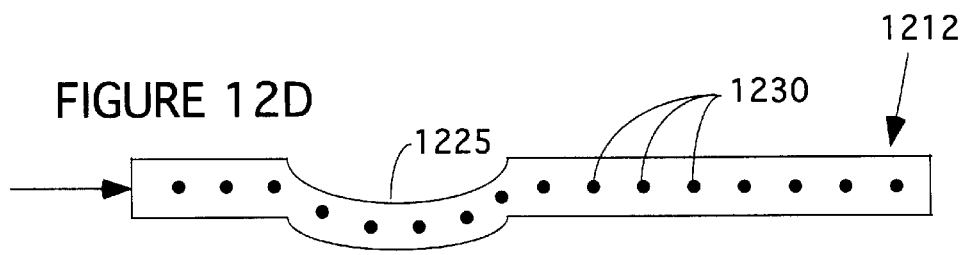

In another preferred arrangement and as is illustrated in FIG. 12D, an array of longitudinal light sensors 1230 measures the amount of light received at each point along the length of device 1212. Obviously, if each of the sensors 1230 is monitored for received light energy, the far sensors will sense decreased light falling thereon at least as a function of the distance the light has traveled from its source. However, when a patient introduces a depression 1255 into the device, light reaching the sensors 1230 located on the other side of the depression 1255 will exhibit a more marked light drop than would have been present in the unoccupied case of FIG. 12A.

Figure 12E:
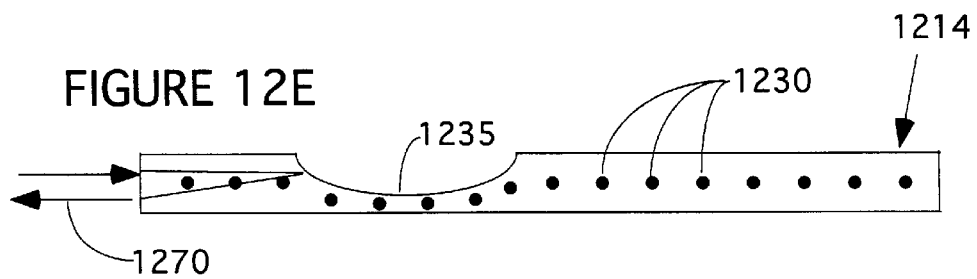

Finally, in a last preferred arrangement, in FIG. 12E the thickness and resiliency of device 1214 is such that a patient at least partially compresses the upper surface toward the lower surface. One way to accomplish this is via the use of two different plastics of different compressibilities, although other arrangements are certainly possible. In the embodiment of FIG. 12E, light that might otherwise travel to the opposite end of the device 1214 is intercepted and reflected by the depression 1235 that is introduced by the weight of the patient. Thus, either the intensity of the reflected light 1270 or the received intensity at the longitudinal receptors 1230 can be used (as has been described above) to determine the location of the patient on the device.

Figure 2:
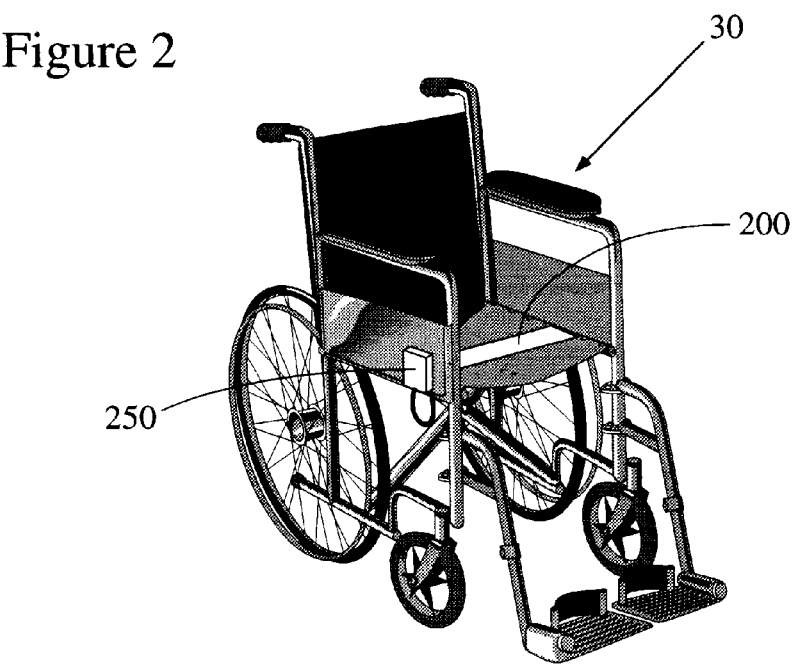
FIG. 2 illustrates a preferred embodiment of the instant invention for use in a wheel chair.

Note that the any of the foregoing mat embodiments could also be placed on chairs, lounges, etc. As is generally illustrated in FIG. 2, mats that are suitable for use with beds 20 can, with some slight modifications well known to those skilled in the art, be adapted for use in wheelchairs 30 and stationary chairs in conjunction with chair monitor 250.

Other Embodiments

Figure 5:
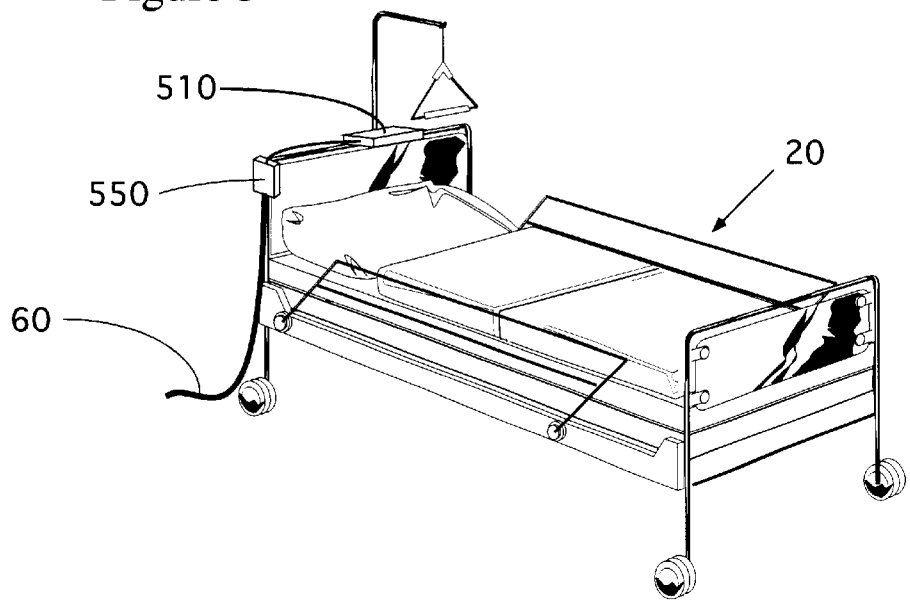
FIG. 5 contains an illustration of another preferred embodiment of the instant invention which utilizes a movement sensor to monitor the position of a patient in the bed.

FIG. 5 contains still another preferred embodiment of the instant invention. In this figure, a motion sensor 510 is positioned above the patient and continuously determines the current patient position and/or historical movement level. The term "continuously" should, of course, be interpreted in its broadest sense to include periodic (i.e., regularly or irregularly time-spaced) re-measurement of the patient's position over some time period. However, in the preferred embodiment, a detector such as an infrared or ultrasonic motion detector will be used and will be continuously pulsed and monitored. This type of monitor would be ideally suited to obtaining a general measure of the patient's movement level over time.

Figure 11:
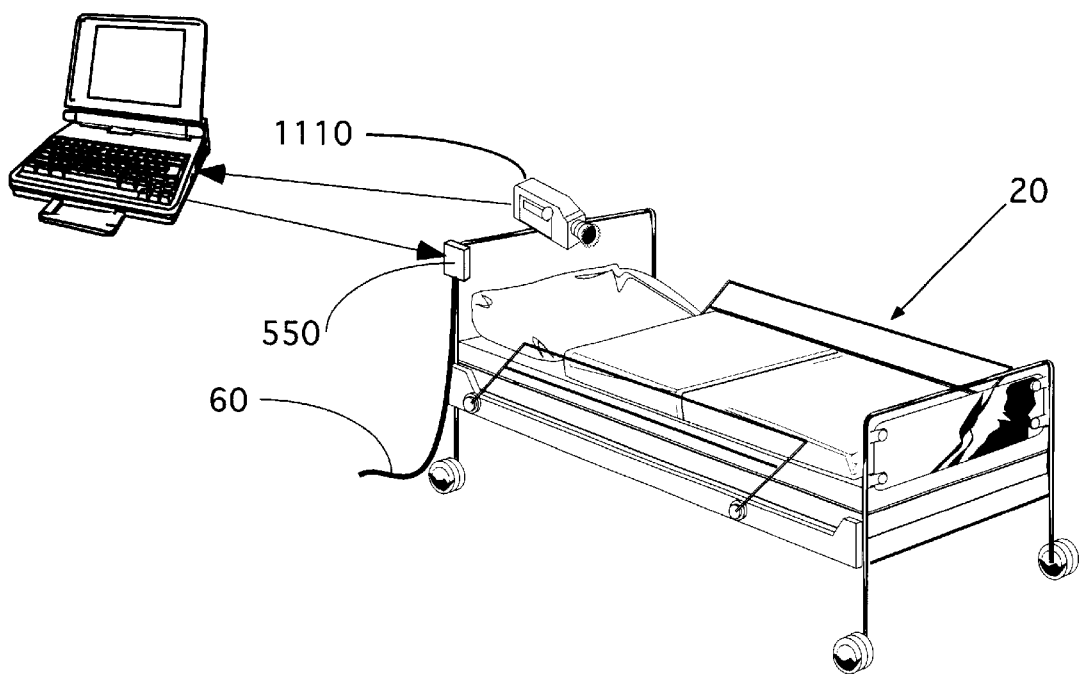
FIG. 11 illustrates another preferred embodiment, wherein the movement sensor is a video camera or similar photographic device.

Another variation of the previous embodiment involves the use of a video camera 1110 or similar photographic device to record the position of the patient (FIG. 11). By converting the patient's video image to digital values and using conventional image processing techniques, it is possible to track the position of a patient and determine when— and by how much—the patient has moved, if he or she moves. Of course, those sorts of mathematical operations might or might not require additional computational power beyond that which might be available within the monitor 50. It is anticipated that a separate computer could be used to process the video information and transmit positional information back to the electronic monitor 550, although other arrangements are certainly possible.

Figure 6:
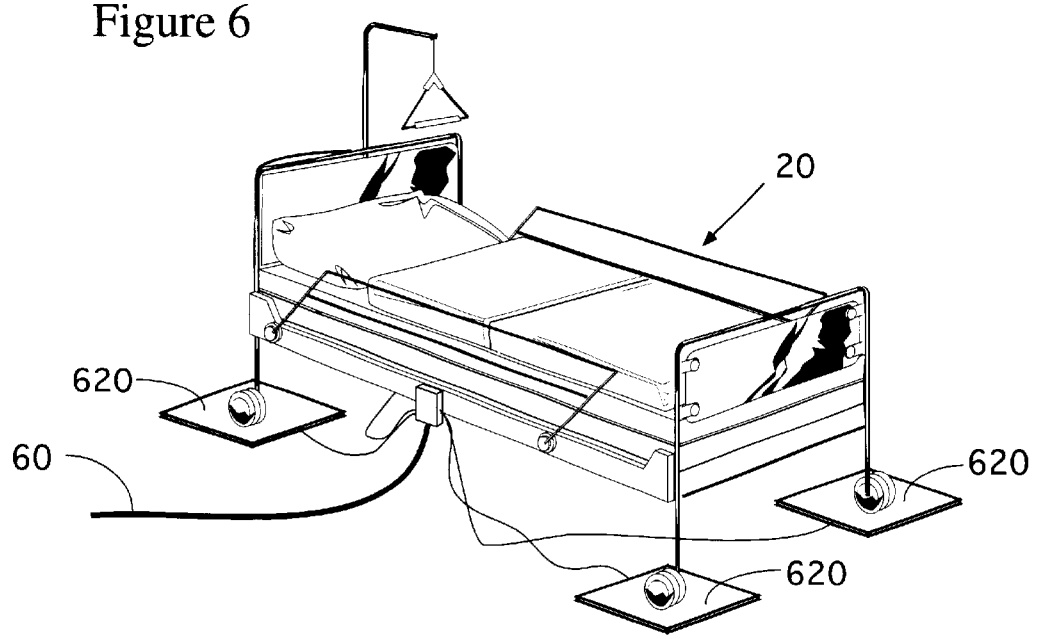
FIG. 6 contains an illustration of still another preferred embodiment of the instant invention which uses pressure sensitive pads positioned under the feet of the bed.

FIG. 6 contains a further preferred embodiment of the instant invention, wherein the legs of the patient's bed have been placed on weight sensing pads 620. As is well known from elementary physics, the amount of weight that is measured on each bed leg will be dependent on the position of the patient in the bed. For example, if the patient has moved toward the left side of the bed, a weight measurement under the left legs will be higher than a weight measurement taken at the same time under the right bed legs. This simple fact can be used to at least roughly estimate the patient's location in the bed, as well as measure the overall time-based activity level of the patient. For example, by measuring the amount of weight change on each leg, it is possible to estimate the distance that the patient's center of gravity has moved. Obviously, this estimate could be used as has been discussed previously to screen for significant movement events, overall activity level, etc. Clearly, this same approach could be used with chair monitors, although it would in all likelihood be impractical for use on a wheel chair. Finally, it should be noted that the instant embodiment could be implemented, albeit somewhat inaccurately, with as few as a single weight sensor positioned under one of the bed legs, provided that certain parameters relating to the dimensions of the bed were known. In the event that a single sensor 620 is used, the CPU 310 would be preferably programmed to determine an initial pre-patient weight force on the single weight sensor 620. Then, after the patient is placed in the bed, the CPU 310 would determine the new weight bearing on the single leg under which the sensor 620 is located. Then, as the patient moves in the bed, that movement will be reflected in changes in the weight bearing on the single sensor 620. That weight change could then be converted at least approximately to movement in the bed.

As a final example of the sort of sensors that would be suitable for use with the instant invention, a further preferred embodiment involves attaching accelerometers to the bed springs of patient's bed. Movement of the patient in the bed translates into vertical motion of the springs that support him or her, with springs that are relieved of weight expanding upward and those supporting additional weight compressing downward. By placing accelerometers that are sensitive to vertical movement at different points, an estimate of the patient's position and historical activity level can readily be obtained.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. An apparatus for reducing the risk of occurrence of decubitus ulcers in a patient at rest on a support surface, wherein is provided a predetermined patient turn interval, comprising:
   (a) a patient location sensor for determining at least approximately an "X" and a "Y" location of the patient on the support surface;
   (b) a time circuit;
   (c) a CPU in electronic communication with said patient location sensor and said time circuit, said CPU at least for
      (c1) determining from said patient location sensor an initial "X" and an initial "Y" location of the patient on the support surface,
      (c2) determining a start time associated with said determination of said initial "X" location and said initial "Y" location,
      (c3) thereafter repeatedly determining from said patient location sensor a then-current "X" location and a then-current "Y" location of the patient on the support surface,
      (c4) determining from said time circuit, said start time, said initial "X" and "Y" locations, and a plurality of said then-current "X" and "Y" locations, a time since the patient last significantly changed location, wherein a significant change of location is one which persists for at least a predetermined time interval, and,
      (c5) initiating a signal indicative of a state of the patient if said time since the patient last significantly changed location is greater than said patient turn interval; and,
   (d) an alarm in electronic communication with said CPU and responsive thereto, said alarm at least for responding to said signal indicative of a state of the patient to produce an alarm signal.

2. An apparatus for reducing the risk of occurrence of decubitus ulcers in a patient according to claim 1, wherein said patient location sensor is a bed mat.

3. An apparatus for reducing the risk of occurrence of decubitus ulcers in a patient according to claim 1, wherein said patient location sensor is a chair mat.

4. An apparatus for reducing the risk of occurrence of decubitus ulcers in a patient according to claim 1, wherein said patient location sensor is selected from a group consisting of a plurality of accelerometers, an infrared sensor, a video camera, and an ultrasonic sensor.

5. An apparatus for reducing the risk of occurrence of decubitus ulcers in a patient according to claim 1, wherein said alarm is a speaker.

6. An apparatus for reducing the risk of occurrence of decubitus ulcers in a patient according to claim 1, wherein said alarm is selected from a group consisting of a light, a buzzer, and a beeper.

7. An apparatus for reducing the risk of occurrence of decubitus ulcers in a patient according to claim 1,
   wherein said apparatus is for use with a bed, said bed having at least four legs, and
   wherein said location sensor includes at least one weight sensor positioned under at least one of said bed legs.

8. An apparatus for reducing the risk of occurrence of decubitus ulcers in a patient according to claim 7, wherein said bed has four legs and wherein said location sensor includes at least four weight sensors, one weight sensor being positioned under each of said four bed legs.

9. An apparatus for reducing the risk of occurrence of decubitus ulcers in a patient according to claim 1, wherein
   said patient location sensor is a mat containing a plurality of sensor points thereon,
   each of said plurality of sensor points being separately readable by said CPU,
   said sensor points being for use in determining at least approximately a location of the patient.

10. An apparatus for reducing the risk of occurrence of decubitus ulcers in a patient according to claim 9, wherein said sensor points are temperature sensors.

11. An apparatus for reducing the risk of occurrence of decubitus ulcers in a patient according to claim 9, wherein said sensor points are piezoelectric elements.

12. A method for reducing the risk of occurrence of decubitus ulcers in a patient at rest on a support surface, comprising the steps of:
   (a) selecting a patient turn interval and a persistence time period said persistence time period being less than said patient turn interval and greater than zero;
   (b) sensing a signal from a patient sensor representative of a first position of the patient on the support surface, wherein said signal representative of the first position of the patient comprises at least an approximate first "X" and first "_Y" location of the patient;
   (c) sensing a signal from said patient sensor representative of a current position of the patient on the support surface wherein said signal representative of said current position of the patient comprises at least an approximate current "X" and current "_Y" location of the patient;
   (d) comparing at least said first "X" and said first "Y" with said current "X" and said current "Y", thereby forming a differential movement measure;
   (e) examining said differential movement measure to determine whether the patient has moved from said first position;
   (f) determining a differential time interval since said signal representative of said first position of the patient was sensed;
   (g) if the patient has not moved from said first position,
      (g1) comparing said differential time interval with said selected turn interval, and,
      (g2) activating an alarm if said differential time interval exceeds said selected turn interval;

(h) if the patient has moved from said first position,
  (h1) monitoring the current patient position to ascertain whether the patient returns at least approximately to said first position within said persistence time period,
  (h2) if the patient does not return at least approximately to said first position within said persistence time period, determining that the patient has moved significantly from said first position,
  (h3) if the patient does return to approximately said first position within said persistence time period,
    (i) comparing said differential time interval with said selected turn interval,
    (ii) activating an alarm if said differential time interval exceeds said selected turn interval, and,
    (iii) performing steps (i) and (ii) until either the patient moves again or until said differential time interval exceeds said selected turn interval; and,
(i) performing steps (b) through (h) as necessary to reduce the risk of occurrence of decubitus ulcers in the patient.

13. A method for reducing the risk of occurrence of decubitus ulcers in a patient according to claim 12, wherein said patient sensor of step (c) is a pressure sensitive mat.

14. A method for reducing the risk of occurrence of decubitus ulcers in a patient according to claim 12, wherein step (e) includes the steps of:
  (e1) examining said differential movement measure to determine whether the patient has moved from said first position, and,
  (e2) determining that the patient has not moved from said first position if said differential movement measure does not exceed a predetermined threshold value.

15. A method for reducing the risk of occurrence of decubitus ulcers in a patient at rest on a support surface, comprising the steps of:
  (a) selecting a patient turn interval;
  (b) selecting a persistence time period less than said patient turn interval and greater than zero;
  (c) determining a first position of the patient on the support surface, said first position comprising at least a first "X" position and a first "Y" position;
  (d) continuously obtaining a position of the patient and continuously determining an elapsed time since said first position was determined,
  (e) repeating step (d) until either a movement of the patient from said first position is detected, or until said determined elapsed time exceeds said selected patient turn interval,
    (e1) if said determined elapsed time exceeds said selected patient turn interval, activating an alarm, else,
    (e2) if the patient moves from said first position,
      (i) continuously monitoring the current patient position to ascertain whether the patient returns at least approximately to said first position within said persistence time period,
      (ii) if the patient does not return at least approximately to said first position within said persistence time period, determining that the patient has moved significantly from said first position,
      (iii) if the patient does return to approximately said first position within said persistence time period,
        (A) comparing said elapsed time with said selected turn interval,
        (B) activating an alarm if said elapsed time exceeds said selected turn interval, and,
        (C) performing steps (A) and (B) until either the patient moves again or until said elapsed time exceeds said selected turn interval; and,
  (f) performing steps (c) through (e) as necessary to reduce the risk of occurrence of decubitus ulcers in the patient.

16. A method for reducing the risk of occurrence of decubitus ulcers in a patient according to claim 15, wherein is provided a movement threshold, and the step of repeating step (d) until movement of the patient from said first position is detected comprises the step of repeating step (d) until movement of the patient from the first position in excess of said movement threshold is detected.

17. An apparatus for reducing the risk of occurrence of decubitus ulcers in a patient, comprising:
  (a) a patient location sensor for determining at least approximately a location of the patient;
  (b) a time circuit;
  (c) a CPU in electronic communication with said patient location sensor and said time circuit, said CPU at least for determining from said time circuit and said patient location sensor a time since the patient last changed location;
  (d) an alarm in electronic communication with said CPU and responsive thereto, said alarm for signaling a state of said patient depending on at least said patient location and said time since the patient last changed location, wherein said patient location sensor is selected from a group consisting of a chair mat, a plurality of accelerometers, an infrared sensor, a video camera, and an ultrasonic sensor.

18. An apparatus for reducing the risk of occurrence of decubitus ulcers in a patient, wherein said apparatus is for use with a bed, said bed having at least four legs, comprising:
  (a) a patient location sensor for determining at least approximately a location of the patient, said location sensor including at least one weight sensor positioned under at least one of said bed legs;
  (b) a time circuit;
  (c) a CPU in electronic communication with said patient location sensor and said time circuit, said CPU at least for determining from said time circuit and said patient location sensor a time since the patient last changed location; and,
  (d) an alarm in electronic communication with said CPU and responsive thereto, said alarm for signaling a state of said patient depending on at least said patient location and said time since the patient last changed location.

19. An apparatus for reducing the risk of occurrence of decubitus ulcers in a patient according to claim 11, wherein said bed has four legs and wherein said location sensor includes at least four weight sensors, one weight sensor being positioned under each of said four bed legs.

20. An apparatus for reducing the risk of occurrence of decubitus ulcers in a patient, comprising:
  (a) a patient location sensor for determining at least approximately a location of the patient;
  (b) a time circuit;
  (c) a CPU in electronic communication with said patient location sensor and said time circuit, said CPU at least for determining from said time circuit and said patient location sensor a time since the patient last changed location; and,
  (d) an alarm in electronic communication with said CPU and responsive thereto, said alarm for signaling a state of said patient depending on at least said patient location and said time since the patient last changed location, wherein, said patient sensor is a mat containing a plurality of sensor points thereon, each of said plurality of sensor points being separately readable by said CPU, said sensor points being for use in determining at least approximately a location of the patient, and wherein said sensor points are selected from a group consisting of temperature sensors and piezo-electric elements.

21. An apparatus for reducing the risk of occurrence of decubitus ulcers in a patient, wherein said patient is at rest on a support surface, comprising:

(a) a patient location sensor for determining at least approximately a location of the patient, wherein said patient location sensor is selected from a group consisting of a chair mat, a plurality of accelerometers, an infrared sensor, a video camera, and an ultrasonic sensor;

(b) a time circuit;

(c) a CPU in electronic communication with said patient location sensor and said time circuit, said CPU at least (c1) for determining from said time circuit and said patient location sensor a time since the patient last significantly changed location, and, (c2) for initiating a signal indicative of a state of the patient depending on at least said patient location and said time since the patient last significantly changed location; and, (d) an alarm in electronic communication with said CPU and responsive thereto, said alarm at least for responding to said signal indicative of a state of the patient to produce an alarm signal.

22. An apparatus for reducing the risk of occurrence of decubitus ulcers in a patient at rest on a support surface, wherein the support surface is a bed, said bed having at least four legs, comprising:

(a) a patient location sensor for determining at least approximately a location of the patient, said location sensor including at least one weight sensor positioned under at least one of said bed legs;

(b) a time circuit;

(c) a CPU in electronic communication with said patient location sensor and said time circuit, said CPU at least (c1) for determining from said time circuit and said patient location sensor a time since the patient last significantly changed location, and, (c2) for initiating a signal indicative of a state of the patient depending on at least said patient location and said time since the patient last significantly changed location; and, (d) an alarm circuit in electronic communication with said CPU and responsive thereto, said alarm circuit at least for responding to said signal indicative of a state of the patient to produce an alarm signal.

23. An apparatus for reducing the risk of occurrence of decubitus ulcers in a patient according to claim 22, wherein said bed has four legs and wherein said location sensor includes at least four weight sensors, one weight sensor being positioned under each of said four bed legs.

24. An apparatus for reducing the risk of occurrence of decubitus ulcers in a patient at rest on a support surface, comprising:

(a) a patient location sensor for determining at least approximately a location of the patient on the support surface, (a1) wherein said patient sensor is a mat containing a plurality of sensor points thereon, (a2) wherein each of said plurality of sensor points is separately readable by said CPU, said sensor points being for use in determining at least approximately a location of the patient on the support surface, and, (a3) wherein said sensor points is are selected from a group consisting of temperature sensors and piezo-electric elements;

(b) a time circuit;

(c) a CPU in electronic communication with said patient location sensor and said time circuit, said CPU at least (c1) for determining from said time circuit and said patient location sensor a time since the patient last significantly changed location, and, (c2) for initiating a signal indicative of a state of the patient depending on at least said patient location and said time since the patient last significantly changed location; and, (d) an alarm circuit in electronic communication with said CPU and responsive thereto, said alarm circuit at least for responding to said signal indicative of a state of the patient to produce an alarm signal.

25. A method for reducing the risk of occurrence of decubitus ulcers in a patient at rest on a support surface, wherein is provided a predetermined movement time period comprising the steps of:

(a) selecting a patient turn interval;

(b) determining a first position of the patient on the support surface;

(c) continuously monitoring a position of the patient and continuously determining an elapsed time since said first position was determined, until either a significant movement of the patient from said first position is detected, or until said determined elapsed time exceeds said selected patient turn interval, (c1) if said significant movement of the patient from said first position is detected, (i) continuing to monitor the patient for a period of time at least as long as said predetermined movement time period, (ii) if the patient moves next to a location substantially the same as said first position before said predetermined movement time period has passed, determining that the patient has not moved, and, (iii) if the patient does not move next to a location substantially the same as said first position before said predetermined movement time period has passed, determining that the patient has moved, and determining anew said first position of the patient;

(c2) if said determined elapsed time exceeds said selected patient turn interval, activating an alarm; and, (d) performing steps (b) and (c) as necessary to reduce the risk of occurrence of decubitus ulcers in the patient.

* * * * *